United States Patent
Stanton et al.

(10) Patent No.: US 6,249,703 B1
(45) Date of Patent: Jun. 19, 2001

(54) HANDHELD PATIENT PROGRAMMER FOR IMPLANTABLE HUMAN TISSUE STIMULATOR

(75) Inventors: David J. Stanton, Oak Grove; Gregory A. Hrdlicka, Plymouth, both of MN (US); Charles M. Meyerson, Scottsdale; Todd A. Kallmyer, Tempe, both of AZ (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 08/272,728

(22) Filed: Jul. 8, 1994

(51) Int. Cl.[7] .................................................. H04B 7/00

(52) U.S. Cl. .............................. 607/30; 607/32; 607/60

(58) Field of Search ............................. 607/27, 28, 30, 607/31, 32, 59, 60, 9; 128/903

(56) References Cited

U.S. PATENT DOCUMENTS

| | | | |
|---|---|---|---|
| 3,311,111 | 3/1967 | Bowers | 128/422 |
| 3,518,997 | 7/1970 | Sessions | 128/422 |
| 3,623,486 | 11/1971 | Berkovits | 128/419 P |
| 3,631,860 | 1/1972 | Lopin | 129/419 P |
| 3,738,369 | 6/1973 | Adams | 128/419 P |
| 3,805,796 | 4/1974 | Terry, Jr. | 128/419 P |
| 4,066,086 | 1/1978 | Alferness | 128/421 |
| 4,208,008 | 6/1980 | Smith | 371/15 |
| 4,211,235 | 7/1980 | Keller, Jr. | 128/419 PG |
| 4,232,679 | 11/1980 | Schulman | 128/419 PG |
| 4,233,985 | 11/1980 | Hartlaub | 128/419 PG |
| 4,236,524 | 12/1980 | Powell | 128/419 PT |
| 4,250,884 | 2/1981 | Hartlaub | 128/419 PT |
| 4,253,466 | 3/1981 | Hartlaub | 128/419 PG |
| 4,273,132 | 6/1981 | Hartlaub | 128/419 PT |
| 4,273,133 | 6/1981 | Hartlalub | 128/419 PG |
| 4,365,633 | * 12/1982 | Loughman et al. | 607/30 |
| 4,374,382 | 2/1983 | Markowitz | 340/870.01 |
| 4,401,120 | 8/1983 | Hartlaub | 128/419 PT |
| 4,539,992 | 9/1985 | Calfee | 128/419 PG |
| 4,550,370 | * 10/1985 | Baker | 607/30 |
| 4,550,732 | 11/1985 | Batty, Jr. | 128/419 PG |
| 4,556,063 | 12/1985 | Thompson | 128/419 PT |
| 4,571,589 | 2/1986 | Slocum | 340/870.32 |

(List continued on next page.)

OTHER PUBLICATIONS

Model 7433 ITREL® II Portable Programmer brochure, Feb. 1992.
Model 9760 Programmer brochure, copyright 1990.

*Primary Examiner*—Kennedy J. Schaetzle
(74) *Attorney, Agent, or Firm*—Curtis D. Kinghorn; Terry L. Wiles; Tom Berry (57) ABSTRACT

A patient programmer for facilitating patient control over an implanted medical device, such as an implanted spinal cord stimulator or the like, is disclosed. A programmer in accordance with the present invention is a portable, light-weight, easy to use patient programmer. The programmer enables a patient to control the operation of his or her implanted device outside of a clinical setting. The programmer incorporates features which ensure that users of varying ages, education levels, dexterity levels, physical and mental health will be able to safely control the operation of their implanted devices, within predefined limits established by a physician or clinician. Circuitry is provided for avoiding battery depletion and/or undesired programmer/implanted device communication in the event that the programmer's key is accidentally depressed (for example, due to being jammed into a purse or pocket) or is depressed repeatedly or continuously over an extended period of time. The programmer provides tactile, audible, and visible feedback to the user to convey information regarding the proper (or improper) operation of the programmer and the implanted device. In one embodiment, the device includes a beeper and light-emitting diodes (LEDs) to indicate, for example, that a desired programming function has been successful or unsuccessful.

15 Claims, 6 Drawing Sheets

U.S. PATENT DOCUMENTS

| | | | |
|---|---|---|---|
| 4,676,248 | 6/1987 | Berntson | 128/419 PG |
| 4,735,204 | 4/1988 | Sussman | 128/419 R |
| 4,793,353 | 12/1988 | Borkan | 128/421 |
| 4,846,180 * | 7/1989 | Buffet | 607/30 |
| 4,941,201 * | 7/1990 | Davis | 607/27 |
| 4,958,632 * | 9/1990 | Duggan | 607/30 |
| 5,052,388 | 10/1991 | Sivula | 128/419 PG |
| 5,127,404 | 7/1992 | Wyborny | 128/419 P |
| 5,179,946 | 1/1993 | Weiss | 128/419 D |
| 5,304,209 * | 4/1994 | Adams et al. | 607/30 |
| 5,331,966 * | 7/1994 | Bennett et al. | 607/28 |

\* cited by examiner

HANDHELD PATIENT PROGRAMMER FOR IMPLANTABLE HUMAN TISSUE STIMULATOR

FIELD OF THE INVENTION

This invention relates generally to the field of body-implantable medical device systems, and more particularly to a programming apparatus for a body-implantable human tissue stimulator.

BACKGROUND OF THE INVENTION

In the medical field, various types of automatic, body-implantable devices are known and commercially-available. One of the more common types of body-implantable devices is the cardiac pacemaker, which operates to deliver electrical stimulating pulses to a patient's heart. A cardiac pacemaker is disclosed, for example, in U.S. Pat. No. 5,052,388 to Sivula et al, entitled "Method and Apparatus for Implementing Activity Sensing in a Pulse Generator." Implantable cardioverters, defibrillators, and drug pumps are other examples of presently available automatic implantable devices. An example of a combination pacemaker/cardioverter/defibrillator is described in U.S. Pat. No. 5,179,946 to Weiss, entitled "Apparatus and Method for Arrhythmia Detection by Variations in the Transcardiac Impedance Between Defibrillation Patches."

It has also been proposed in the prior art to provide implantable tissue stimulators for controlling nerve or muscle response, for alleviating pain, or to treat various neurological and/or physiological disorders, such as cerebral palsy, epilepsy, and the like. Examples of such devices are discussed in the following U.S. patents: U.S. Pat. No. 4,232,679 to Schulman, entitled "Programmable Human Tissue Stimulator;" U.S. Pat. No. 4,735,204 to Sussman et al., entitled "System for Controlling an Implanted Neural Stimulator;" and in U.S. Pat. No. 4,793,353 to Borkan, entitled "Non-Invasive Multiprogrammable Tissue Stimulator and Method. " A commercially-available example of an implantable tissue stimulator is the Model 7425 Itrel™ 3 Implantable Pulse Generator, manufactured by Medtronic, Inc., Minneapolis, Minn. The Itrel™ 3 is a spinal cord stimulating system prescribed to alleviate chronically-recurring pain.

It is very common for automatic implantable devices to be non-invasively controllable by means of an external programming apparatus of some sort, so that an implanted device's operational modes and/or parameters may be adjusted, for example to optimize its therapeutic efficacy or in response to post-implant changes in a patient's condition. Often, such non-invasive control is exercised by a physician in a clinical setting.

Perhaps one of the simplest arrangements for facilitating non-invasive control of an implanted device involves providing a magnetic reed switch in the implantable device. After implant, the reed switch can be actuated (closed) by placing a magnet over the implant site. Reed switch closure may then be used, for example, to alternately activate and deactivate the device. Alternatively, some variable parameter of the device (e.g., the pacing rate of an implantable cardiac pacemaker) can be adjusted up or down by incremental amounts based upon the duration of the reed switch closure interval. Many different schemes utilizing a reed switch to adjust operational parameters of medical devices have been developed. See, for example, U.S. Pat. No. 3,311,111 to Bowers; U.S. Pat. No. 3,518,997 to Sessions; U.S. Pat. No. 3,623,486 to Berkovits; U.S. Pat. No. 3,631,860 to Lopin; U.S. Pat. No. 3,738,369 to Adams et al., U.S. Pat. No. 3,805,796 to Terry, Jr.; U.S. Pat. No. 4,066,086 to Alferness et al.; and the above-reference U.S. Pat. No. 4,735,204 to Sussman et al.

Although the relatively simple reed-switch closure arrangement is suitable for the purposes of controlling or adjusting a limited number of operational parameters or modes of an implanted device, it has proven beneficial to provide a means for more efficiently communicating programming information to an implanted device, so that a greater number of the device's operating modes and parameters can be adjusted. In state-of-the-art cardiac pacemakers, for example, a partial list of the types of programmable parameters includes: upper and lower pacing rate limits, stimulating pulse width and/or amplitude, sense amplifier sensitivity, pacing mode, activity- or rate-response settings (e.g., pacing rate acceleration and deceleration, activity threshold, activity detection criteria, and the like), A-V delay times, refractory and blanking periods, and so on. It has also proven desirable for implanted devices themselves to be able to communicate information to an external programming apparatus.

In response to the foregoing considerations, various telemetry systems for providing the necessary communications channels between an external unit and an implanted device have been developed. Telemetry systems are disclosed, for example, in the following U.S. patents: U.S. Pat. No. 4,539,992 to Calfee et al. entitled "Method and Apparatus for Communicating With Implanted Body Function Stimulator"; U.S. Pat. No. 4,550,732 to Batty Jr. et al. entitled "System and Process for Enabling a Predefined Function Within An Implanted Device"; U.S. Pat. No. 4,571,589 to Slocum et al. entitled "Biomedical Implant With High Speed, Low Power Two-Way Telemetry"; U.S. Pat. No. 4,676,248 to Berntson entitled "Circuit for Controlling a Receiver in an Implanted Device"; U.S. Pat. No. 5,127,404 to Wyborny et al. entitled "Telemetry Format for Implanted Medical Device"; U.S. Pat. No. 4,211,235 to Keller, Jr. et al. entitled "Programmer for Implanted Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above-referenced patents are employed in conjunction with an external programming/processing unit. One programmer for non-invasively programming a cardiac pacemaker is described in its various aspects in the following U.S. patents to Hartlaub et al., each commonly assigned to the assignee of the present invention and each incorporated by reference herein: U.S. Pat. No. 4,250,884 entitled "Apparatus For and Method Of Programming the Minimum Energy Threshold for Pacing Pulses to be Applied to a patient's Heart"; U.S. Pat. No. 4,273,132 entitled "Digital Cardiac Pacemaker with Threshold Margin Check"; U.S. Pat. No. 4,273,133 entitled Programmable Digital Cardiac Pacemaker with Means to Override Effects of Reed Switch Closure"; U.S. Pat. No. 4,233,985 entitled "Multi-Mode Programmable Digital Cardiac Pacemaker"; U.S. Pat. No. 4,253,466 entitled "Temporary and Permanent Programmable Digital Cardiac Pacemaker"; and U.S. Pat. No. 4,401,120 entitled "Digital Cardiac Pacemaker with Program Acceptance Indicator".

Aspects of the programmer that is the subject of the foregoing Hartlaub et al. patents (hereinafter "the Hartlaub programmer") are also described in U.S. Pat. No. 4,208,008 to Smith, entitled "Pacing Generator Programming Apparatus Including Error Detection Means" and in U.S. Pat. No. 4,236,524 to Powell et al., entitled "Program Testing Apparatus". The Smith '008 and Powell et al. '524 patents are also incorporated by reference herein in their entirety.

Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modelled as an air-core coupled transformer. Examples of such a telemetry system are shown in the above-referenced Thompson et al. '063 and Hartlaub et al. '120 patents.

In order to communicate digital data using RF telemetry, a digital encoding scheme such as is described in U.S. Pat. No. 5,127,404 to Wyborny et al. entitled "Improved Telemetry Format" is used. In particular, for downlink telemetry a pulse interval modulation scheme may be employed, wherein the external programmer transmits a series of short RF "bursts" or pulses in which the during of an interval between successive pulses (e.g., the interval from the trailing edge of one pulse to the trailing edge of the next) encodes the data. In particular, a shorter interval encodes a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen position data frame may be defined, wherein a pulse in one of the time slots represents a unique four bit portion of data. The Wyborny et al. '404 patent is hereby incorporated by reference herein in its entirety.

Programming units such as the above-described Hartlaub et al. programmer typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

State-of-the-art implantable medical device programmers, as exemplified by the Model 9760 programming unit, manufactured by Medtronic, Inc., Minneapolis, Minn., facilitate the non-invasive control of a full range of operational and diagnostic functions of implanted devices. Accordingly, such programming units are typically used by physicians or other medical personnel in a clinical setting, so that the patient's condition can be carefully monitored during the programming session. Those of ordinary skill in the art will appreciate, however, that in some cases it may be desirable to provide means for allowing the patient to exercise some degree of control over device operation, even outside of the clinical setting. It is desirable, for example, for a patient with an implanted spinal cord stimulation system to be able to trigger the device to deliver a stimulating pulse whenever the patient experiences an episode of pain that the device is intended to alleviate.

To address the need for patient control of an implanted device, so-called patient programmers, such as the Medtronic Model 7433, were developed. The Model 7433 was designed to facilitate patient control over Medtronic implantable tissue stimulators. In operation, the Model 7433 was placed over the implant site and a downlink telemetry link was established, whereby a single cycle of stimulation could be initiated by the patient.

Although the Model 7433 patient programmer has proven satisfactory for its intended purpose, it is believed that the present invention represents an advancement over the prior art, as exemplified by the Model 7433, in several aspects. In particular, it is believed that no prior art programmer intended for use by patients, has incorporated features in recognition of factors such as the varying characteristics of potential patients who will use a patient programmer, including such potential patients' age, education, dexterity, and physical and mental health.

SUMMARY OF THE INVENTION

Accordingly, the present invention relates to a patient programmer for facilitating patient control over an implanted medical device, such as an implanted spinal cord stimulator or the like.

In accordance with the present invention, a portable, light-weight, easy to use patient programmer is provided for enabling a patient to control the operation of his or her implanted device outside of a clinical setting.

The programmer in accordance with the disclosed embodiment of the invention incorporates features which make it easier for users of varying ages, education levels, dexterity levels, physical and mental health to safely control the operation of their implanted devices, within predefined limits established by a physician or clinician.

In accordance with one aspect of the invention, circuitry is provided for avoiding battery depletion and/or undesired programmer/implanted device communication in the event that the programmer's key is accidentally depressed (for example, due to being jammed into a purse or pocket) or is depressed repeatedly or continuously over an extended period of time.

In accordance with another aspect of the invention, the programmer provides tactile, audible, and visible feedback to the user to convey information regarding the proper (or improper) operation of the programmer and the implanted device. For example, the device includes a beeper and light-emitting diodes (LEDs) to indicate, for example, that a desired programming function has been successful or unsuccessful.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Mechanical Description

Figure 1:
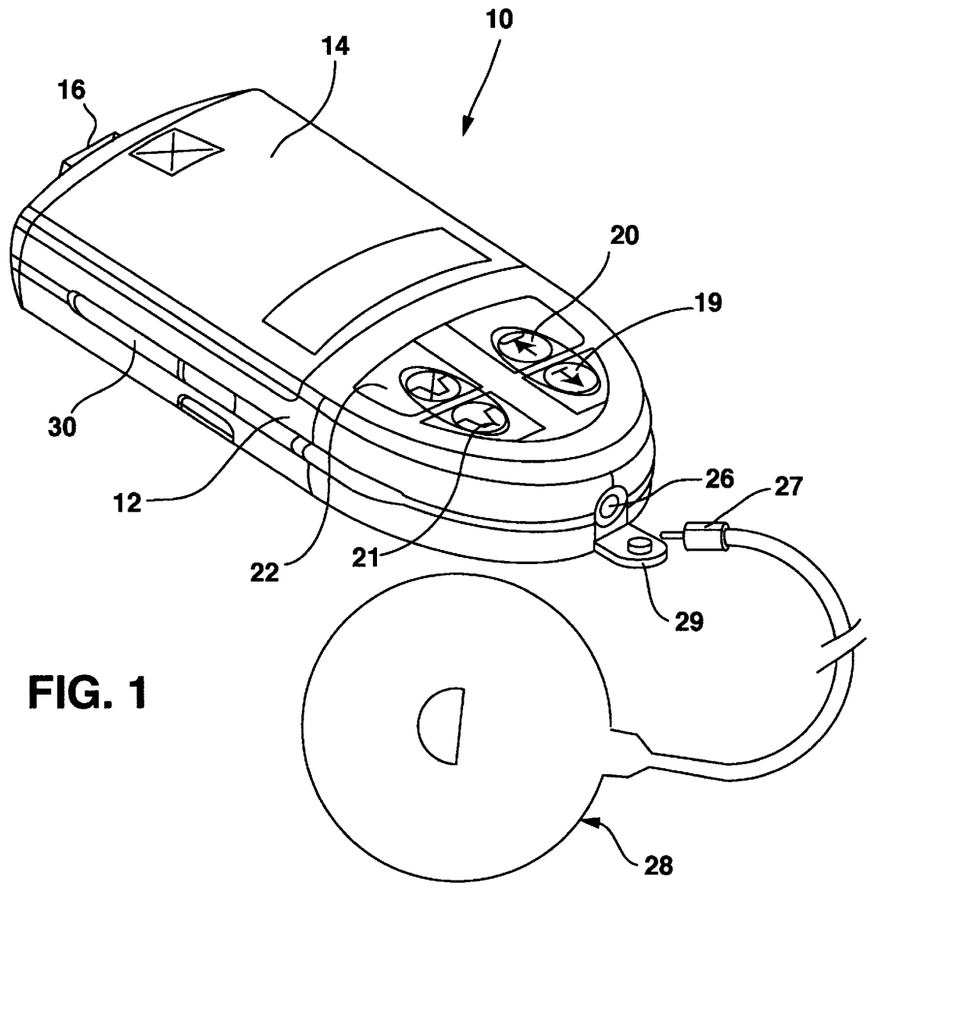
FIG. 1 is a perspective view of a handheld patient programmer in accordance with one embodiment of the present invention.

Referring to FIG. 1, there is shown a perspective view of a patient programmer 10 in accordance with one embodiment of the present invention. Programmer 10 is a small, handheld, battery-powered programming device for use by implantable device patients to control and monitor the operation of their implanted devices. The disclosed embodiment is believed to be suitable, for example, for use in programming a Medtronic Model 7425 Itrel™ 3 implantable spinal cord stimulation system.

As will be hereinafter described in greater detail, programmer 10 includes a downlink radio-frequency (RF) transmitter for transmitting programming signals to an implanted pulse generator (not shown in FIG. 1), and an uplink RF receiver to monitor the programming process and pulse generator status. Programmer 10 may be used, in the presently disclosed embodiment of the invention, to turn the pulse generator on and off, similar to the magnet function of prior art implanted devices, as described above. Unlike magnet/reed switch configurations, however, programmer 10 can also function to allow the patient to adjust amplitude, rate, and pulse width within lower and upper limits which are programmed into the implanted device by the physician using a physician programmer, such as the above-described Model 9760 or Hartlaub programmers. In this sense, those of ordinary skill in the art will appreciate that programmer 10 in accordance with the present invention is not intended as a substitute for a conventional physician programmer. Programmer 10 may have fewer or different programming capabilities than a physician programmer.

In the embodiment shown, the uplink RF receiver in programmer 10 permits monitoring of the implanted device's battery depletion level, and the implanted device's on/off status. In other embodiments it could also indicate other status conditions or physiological parameters of the user.

Figure 2:
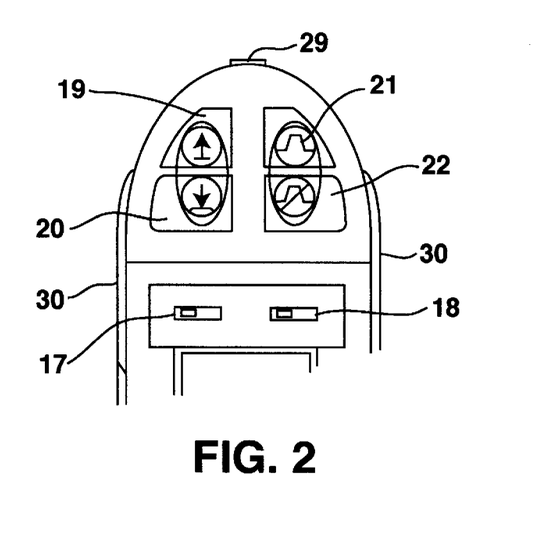
FIG. 2 is a top view of a front portion of the programmer from FIG. 1, with the battery compartment cover removed.

With continued reference to FIG. 1, programmer 10 comprises a main outer housing 12, which is preferably made of injection-molded ABS and polycarbonate, hard plastic, or another suitably rugged material so as to be light-weight, yet not be easily damaged when carried by a patient, for example in a purse or pocket, or even dropped onto the floor. A battery compartment cover 14 is disposed on a top surface of programmer 10. A clip 16 or other fastening mechanism may be disposed on a back end of programmer 10, to facilitate opening of the battery compartment for battery replacement. FIG. 2 is a partial top view of programmer 10 with battery compartment cover 14 removed. As shown in FIG. 2, also disposed within the battery compartment and protected by battery compartment cover 14 is a parameter control switch 17 and a volume control switch 18, the functions of which to be hereinafter described in greater detail.

As shown in FIGS. 1 and 2, a plurality of user keys 19, 20, 21, and 22 are disposed on the upper surface of programmer 10, the functions of which will be hereinafter described in greater detail with reference to later Figures. Keys 19, 20, 21, and 22 preferably have a mechanical detail to give sensory indication to the user when sliding a finger from one key to another.

On the front end of programmer 10, an external antenna jack 26 is provided for receiving a connector 27 from an optional external antenna 28. A flip-down cap 29 is provided to protect antenna jack 26 when no external antenna is used. The use of external antenna 28 eliminates the need to place programmer 10 over the implant site during patient programming sessions. This can be helpful for a patient who cannot easily reach his or her implant site, due either to the patient's physical condition or to the location of the implant site. Antenna 28 may be provided with an adhesive disc so that it may be affixed stably over the implant site during a patient programming session.

As will be appreciated by those of ordinary skill in the art, the overall configuration of programmer 10 is generally smooth and curved so as to fit comfortably in a patient's hand, with keys 19, 20, 21, and 22 being readily accessible on the programmer's upper surface. Disposed along each side of housing 12 are resilient finger grips 30 (only one of which is visible in the view of FIG. 1), which further facilitate comfortable and stable gripping by the patient.

Figure 3:
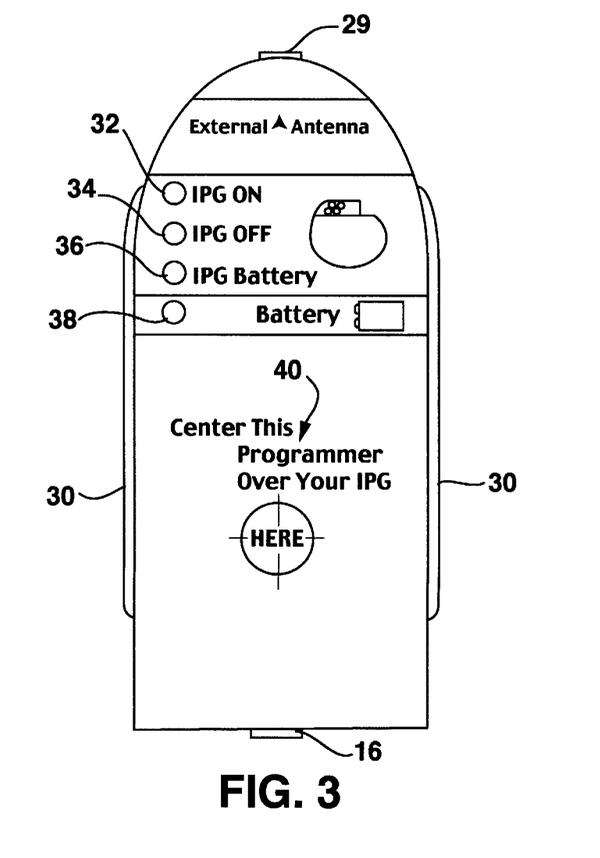
FIG. 3 is a bottom view of the programmer from FIG. 1.

On the underside of programmer 10, which is illustrated in the bottom view of FIG. 3, are disposed a plurality of light-emitting diodes (LEDs) 32, 34, 36, and 38. (Those of ordinary skill in the art will appreciate that LEDs 32, 34, 36, and 38 are preferably disposed within housing 12 and are merely visible through translucent windows in housing 12. For simplicity, reference numerals 32, 34, 36, and 38 will be used herein to refer to the individual LEDs which are visible on the underside of programmer 10 due to this conventional arrangement.) LEDs 32, 34, 36, and 38 are implanted device and programmer status indicators, as will be hereinafter described in greater detail.

Figure 4:
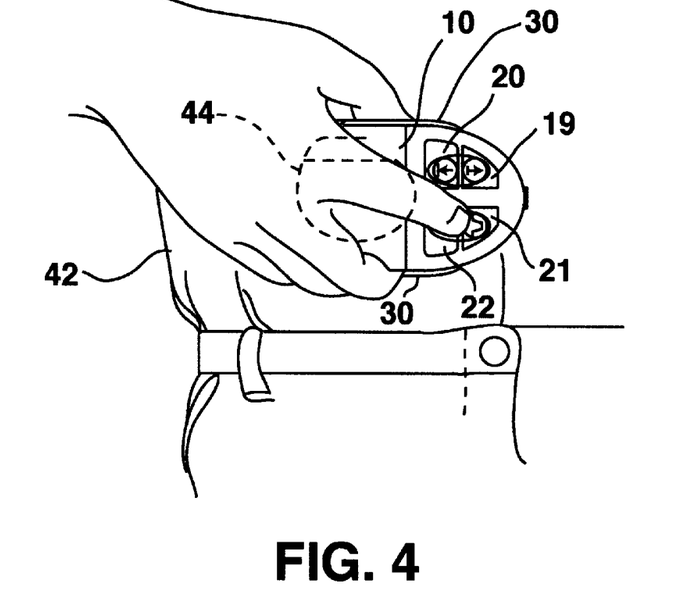
FIG. 4 is an illustration of the programmer from FIG. 1 being placed over a patient's implant site.
Figure 5:
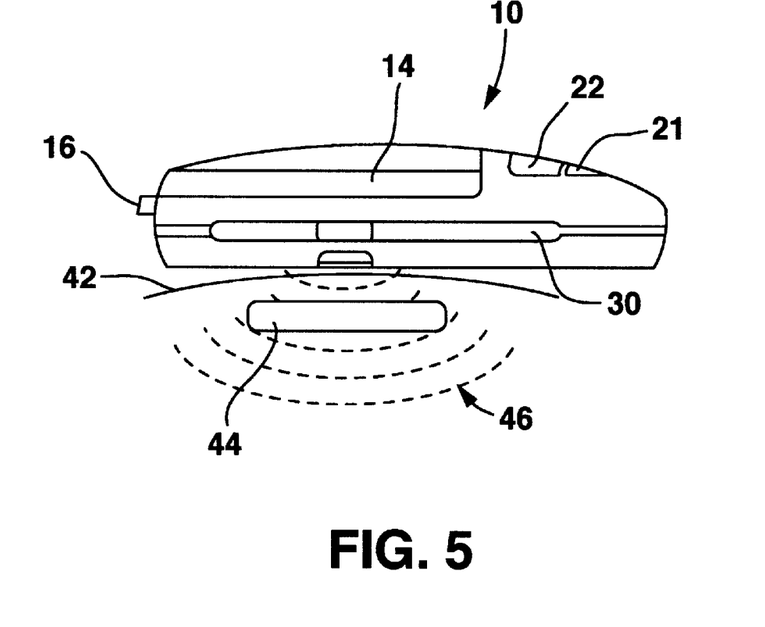
FIG. 5 is a side view of the programmer from FIG. 1 as it is placed over a patient's implant site.

Also shown in FIG. 3 is a "cross-hair" diagram and associated legend, designated generally with reference numeral 40, which are imprinted on the underside of programmer 10 to assist the patient in proper positioning of programmer 10 over the implant site during a patient programming session. Legend 40, which reads, e.g., "Center This Programmer Over Your IPG, " instructs the patient where to place programmer 10 so that uplink RF signals transmitted from an implanted device can be received by the internal antenna (not shown) of programmer 10, and conversely so that downlink telemetry signals transmitted from programmer 10 can be received by the implanted device's internal antenna. This is depicted in FIGS. 4 and 5, wherein a patient 42 has placed programmer 10 against his or her body over the implant site of a device 44 in a conventional lower abdominal region of patient 42. Downlink RF telemetry signals are represented by dashed lines 46 in FIG. 5.

Electrical Description

Figure 6:
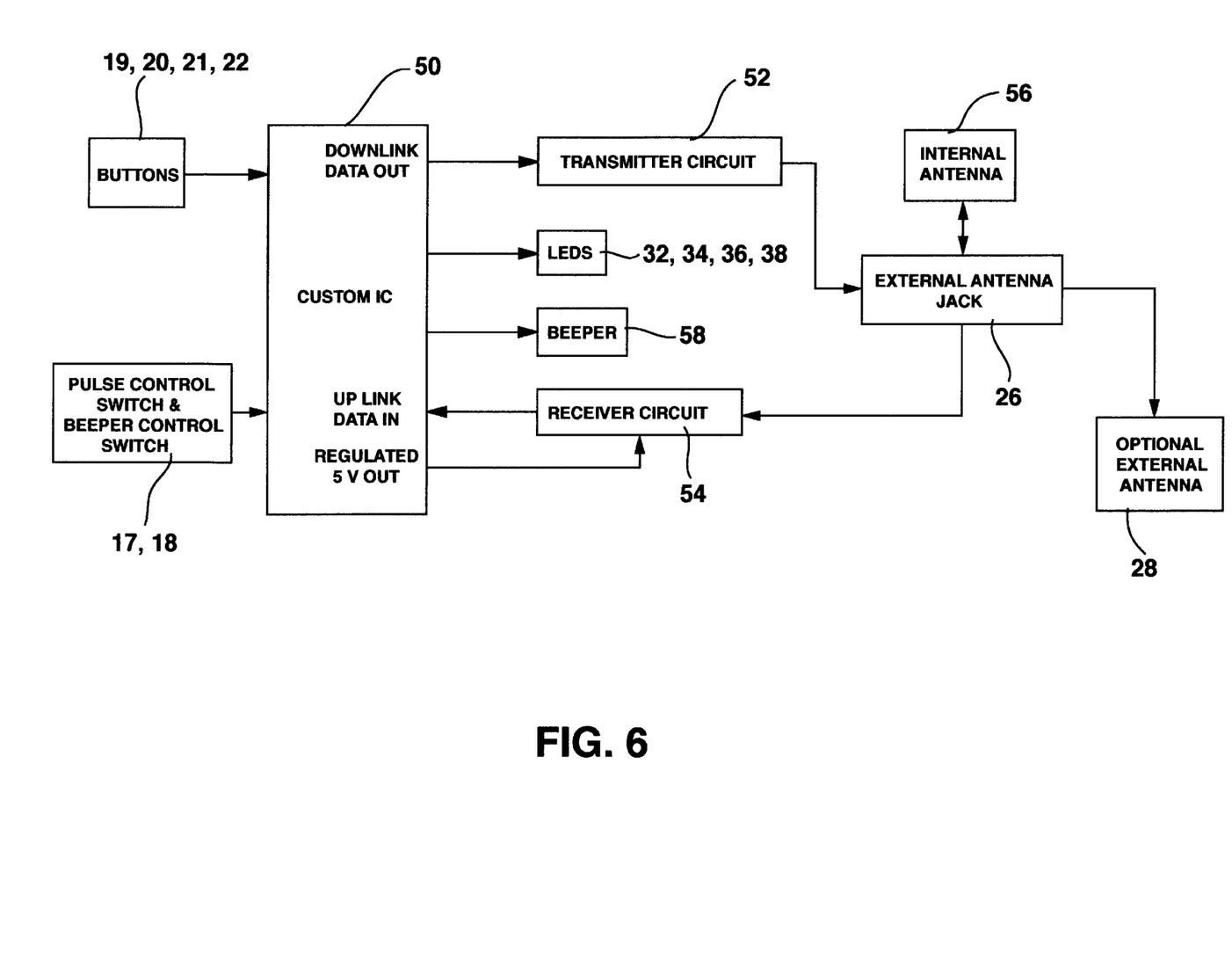
FIG. 6 is a block diagram of circuitry within the programmer from FIG. 1.

Turning now to FIG. 6, there is shown a block diagram of the internal circuitry of programmer 10. At the heart of the circuitry represented in FIG. 2 is a custom integrated circuit (IC) 50 to be hereinafter described in greater detail. As shown in FIG. 2, keys 19, 20, 21, and 22 are coupled to inputs of IC 50, as are pulse control switch 17 and beeper control switch 18.

As previously noted, programmer 10 includes a downlink telemetry RF transmitter, designated with reference numeral 52 in FIG. 6, and an uplink telemetry RF receiver, designated with reference numeral 54 in FIG. 6. Transmitter circuit 52 is coupled to a DOWNLINK DATA OUT terminal of IC 50, while receiver circuit 54 is coupled to an UPLINK DATA IN terminal of IC 50. The output from transmitter circuit 52 is applied to an internal antenna 56 via external antenna jack 26 previously noted with reference to FIG. 1. Optional external antenna 28, previously described with reference to FIG. 1 is also removably coupled to antenna jack 26. The connection between transmitter circuit 52 and internal antenna 56 is made via antenna jack 26, to facilitate the disabling of internal antenna 56 when external antenna 28 is plugged into jack 26, in accordance with common practice in the art.

Antenna jack 26 is also coupled to an input of receiver circuit 54, so that uplink telemetry signals received by internal antenna 56 (or by external antenna 28) may be applied thereto. Uplink telemetry signals received by receiver circuit 54 are then applied to the UPLINK DATA IN terminal of IC 50.

A beeper, designated with reference numeral 58 in FIG. 6, is coupled to IC 50 to receive a control signal therefrom. Beeper 58 provides an audible indication of certain programming events, as will be hereinafter described in greater detail.

A 9-volt battery, housed within the battery compartment of programmer 10 previously described with reference to FIG. 1, is coupled to respective power inputs (not shown) of IC 50, transmitter circuit 52, receiver circuit 54, LEDs 32, 34, 36, and 38, and beeper 58. For simplicity, the connections between the battery and these elements are not shown in FIG. 6. IC 50 includes voltage regulation circuitry, so that it can provide a regulated five volt output signal to receiver circuit 54.

Figure 7:
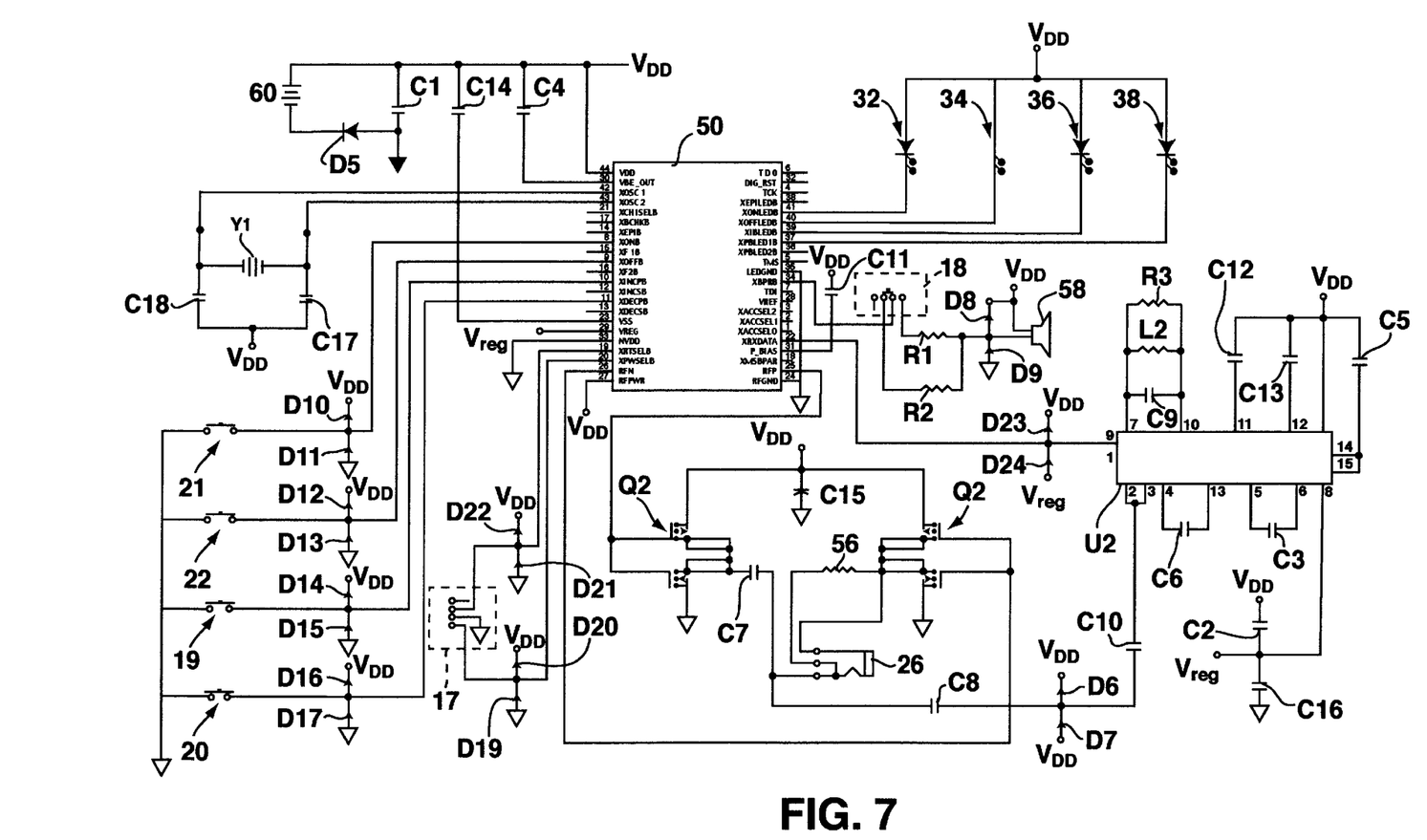
FIG. 7 is a schematic diagram of the circuitry within the programmer from FIG. 1.

Turning now to FIG. 7, there is shown a more detailed schematic diagram of the internal circuitry shown in block diagram form in FIG. 6. Elements of FIG. 7 which are identical to those discussed with reference to FIG. 6 have retained identical reference numerals in FIG. 7. The 9-volt battery described with reference to FIG. 6 is identified with reference numeral 60 in FIG. 7. In the following Table 1, there is set forth a component listing for the components shown in the schematic diagram of FIG. 7, along with their respective component values:

TABLE 1

| COMPONENT | VALUE |
| --- | --- |
| C1 | 0.1 μF |
| C2 | 0.1 μF |
| C3 | 0.01 μF |
| C4 | 1800 μF |
| C5 | 0.1 μF |
| C6 | 0.047 μF |
| C7 | 0.033 μF |
| C8 | 0.001 μF |
| C9 | 1800 μf |
| C10 | 0.01 μf |

TABLE 1-continued

| COMPONENT | VALUE |
| --- | --- |
| C11 | 0.1 μf |
| C12 | 0.001 μf |
| C13 | 0.01 μf |
| C14 | 0.1 μf |
| C15 | 10 μf (tantalum) |
| C16 | 0.1 μf |
| C17 | 33 pF |
| C18 | 33 pF |
| R1 | 200Ω |
| R2 | 432Ω |
| R3 | 430Ω |
| D1–D4, D6–D24 | DIODES |
| D5 | LL103 SCHOTTKY |
| L2 | 420 μH |
| Q1 | S19952DY |
| Q2 | S19952DY |
| Y1 | 5.6MHz OSC. |
| U2 | TDA3047 IC |

As shown in FIG. 7, Beeper Switch 18 disposed within the battery compartment of programmer 10 is a three-position switch for enabling the user to turn the beeper off or select one of two resistors (R1 and R2 in FIG. 7) for volume settings for beeper 58. Parameter Select Switch 17, also disposed within the battery compartment, is a three-position switch for defining the function of INC and DEC keys 19 and 20. Depending upon the position of switch 17, INC and DEC keys 19 and 20 function to increase and decrease, respectively, the amplitude, rate, or pulse width of stimulating pulses delivered by implanted device 44.

IC 50 is sequenced by a 5.6 MHz clock. The oscillator time base is an external ceramic resonator designated as Y1 in FIG. 7. Capacitors C17 and C18 required for resonator Y1 are preferably on-chip in mask-programmable form, selectable up to 32-pF. External capacitors may also be used for fine-tuning.

Integrated Circuitry

Regarding custom IC 50, in the presently preferred embodiment of the invention, it is implemented as a logic state-machine controller which generates a serial bit pattern for RF downlink telemetry with data retrieved from an on-board ROM. IC 50 provides drive signals to LED 38. IC 50 also provides drive signals to LEDs 32, 34, and 36, and to beeper 58 based upon serial bit patterns received as uplink transmissions from implanted device 44. Uplink telemetry signals are demodulated by an integrated circuit designated as U2 in FIG. 7.

Figure 8:
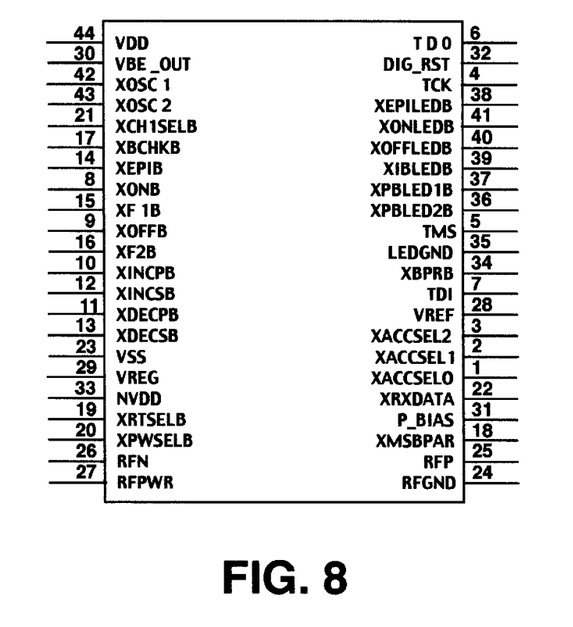
FIG. 8 is a pinout diagram of an integrated circuit in the circuitry from FIG. 7.

With reference now to FIG. 8, which shows IC 50 from the circuit of FIG. 7 in isolation, the following Table 2 sets forth the pin definition for IC 50:

TABLE 2

| PIN NO. | SYMBOL | DESCRIPTION |
| --- | --- | --- |
| 1 | XACCSEL0 | Access code select pin. To be at Vdd or left open via PC board layout. This pin, in conjunction with XACCSEL1 and XACCSEL2, will select pulse generator access codes. This pin to be binary least significant bit (LSB). Internal pulldown to Vss. |
| 2 | XACCSEL1 | Access code select pin. To be at Vdd or left open via PC board layout. This pin, in conjunction with XACCSEL0 and XACCSEL2, will select pulse generator access codes. Internal pulldown to Vss. |

TABLE 2-continued

| PIN NO. | SYMBOL | DESCRIPTION |
| --- | --- | --- |
| 3 | XACCSEL2 | Access code select pin. To be at Vdd or left open via PC board layout. This pin, in conjunction with XACCSEL0 and XACCSEL1, will select pulse generator access codes. This pin to be binary most significant bit (MSB). Internal pulldown to Vss. |
| 4 | TCK | Test pin. TAP controller test clock input. Internal pullup to Vdd |
| 5 | TMS | Test pin. TAP controller machine state control. Internal pullup to Vdd |
| 6 | TDO | Test pin. TAP controller data output. |
| 7 | TDI | Test pin. TAP controller data input. Internal pullup to Vdd |
| 8 | XONB | Keyboard input pin. When at NVdd, provides ON code downlink signal. Internal pullup to Vdd. |
| 9 | XOFFB | Keyboard input pin. When at NVdd, provides OFF code downlink signal. |
| 10 | XINCPB | Keyboard input pin. Implanted device 44 will respond to the INC command only if in the IPG ON state. When at NVdd, this pin provides CH 1 INC code downlink signal for parameter selected by state of XRTSELB and XPWSELB per the following:<br><br>PARAMETER   PIN 20   PIN 21<br><br>AMPLITUDE   1   1<br>RATE   0   1<br>PULSE WIDTH   1   0<br>(0 = NVdd, 1 = Vdd) |
| 11 | XDECPB | Keyboard input pin. When at NVdd, provides DEC downlink signal for parameter selected by the state of XRTSELB and XPWSELB to downlink as for XINCPB (see description for pin 10 above). Internal pullup to Vdd. |
| 12 | XINCSB | Reserved for future functions. |
| 13 | XDECSB | Reserved for future functions. |
| 14 | XEPIB | Reserved for future functions. |
| 15 | XF1B | Reserved for future functions. |
| 16 | XF2B | Reserved for future functions. |
| 17 | XBCHKB | Reserved for future functions. |
| 18 | XMSBPAR | Reserved for future functions. |
| 19 | XRTSELB | Input pin to select Rate (see description of XINCPB pin 10 above). Internal pullup to Vdd. |
| 20 | XPWSELB | Input pin to select Pulse Width (see description of XINCPB pin 10 above). Internal pullup to Vdd. |
| 21 | XCH1SELB | Reserved for future functions. |
| 22 | XRXDATA | Receive uplink data input from RF demodulator IC U2. |
| 23 | VSS | Negative logic power supply pin brought out for capacitor filter. Vss = Vdd − (1.4 ± 0.3 volts) |
| 24 | RFGND | Negative battery input (NVdd) for driving RFP and RFN outputs. |
| 25 | RFP | Pulse interval modulated 175 kHz, RF output from IC 50. Used to drive external RF output transistors Q1 and Q2. Output must switch between Vdd and NVdd supply rails. During uplink reception, this pin is at NVdd. Inverse of XRFN. |
| 26 | RFN | Inverse of XRFP. |
| 27 | RFPWR | Positive battery input (Vdd) for driving RFP and RFN outputs. |
| 28 | VREF | VREG filter/oxide stress test. |
| 29 | VREG | Switched, regulated, negative power supply for external receiver IC U2. Regulated at 5 volts referenced to Vdd. Capable of sinking 3 mA. |
| 30 | VBE_OUT | Internal power supply pin brought out for capacitor filter. |
| 31 | PBIAS | Internal power supply pin brought out for capacitor filter. |
| 32 | DIG_RST | Test pin, input. Resets functional digital logic. Internal pulldown to Vss. |
| 33 | NVDD | Negative 9 volt battery power supply pin. |
| 34 | XBPRB | Beeper driver output. Provides an open drain FET that sinks beeper current to NVdd to activate beeper. |
| 35 | LEDGND | NVdd power supply pin for LEDs 32, 34, 36, and 38. |
| 36 | XPBLED2B | LED output identical in function to XPBLED1B (pin 37 below). |

TABLE 2-continued

| PIN NO. | SYMBOL | DESCRIPTION |
|---|---|---|
| 37 | XPBLED1B | Low battery indicator. Turns on, or blinks, for six seconds upon any patient key depression if the battery is good or low, respectively. LED indication triggered by any key push, regardless of the presence of uplink signal. LED to remain off if programmer battery is at or below end-of-life (EOL) |
| 38 | XEPILEDB | Reserved for future functions. |
| 39 | XIBLEDB | Indicator LED for status of implanted device's battery. Turns on, or blinks, for six seconds, each time the RXDATA indicates that the implanted device's battery is good or low, respectively. LED to remain off if implanted device's battery is at or below EOL. |
| 40 | XOFFLEDB | LED for indicating that implanted device 44 is off. Turns on for six seconds each time the RXDATA indicates that implanted device 44 is off. |
| 41 | XONLEDB | LED for indicating that implanted device 44 is on. Turns on for six seconds each time the RXDATA indicates that implanted device 44 is on. |
| 42 | XOSC1 | Input pin for crystal or ceramic oscillator Y1 to control frequency of IC oscillator. Frequency = 5.6 MHz (an integer multiple of 175 KHz to enable same oscillator to generate system clock and RF data pulse drive. |
| 43 | XOSC2 | See description for XOSC1 above. |
| 44 | VDD | Positive 9 volt power supply pin. Vdd is considered to be chip ground. |

In accordance with one aspect of the present invention, an on-chip "watchdog timer" counts successive bad uplinks generated during one continuous keypress of any key. This detects a key that is held pressed for an extended period of time, for example if programmer 10 is jammed into a user's pocket or purse. When 32 consecutive bad uplinks (i.e., no valid uplinks) are counted, which would occur if a key depressed when programmer 10 is not near the implant site for a predetermined period of time, LEDs 32, 34, 36, and 38 are deactivated, and downlink telemetry transmissions are terminated. Also, the regulated voltage Vreg is turned off to power-down the receiver IC U2. This conserves programmer battery life. Operation is restored 400 milliseconds after the release of all keys.

Further in accordance with the presently disclosed embodiment of the invention, upon the next keypress after a watchdog shutdown, the watchdog timer in IC 50 operates to cause a shutdown after only eight bad uplinks corresponding to a second predetermined period of time, unless a good uplink is received. This further limits battery drain due to intermittent keypresses due to programmer 10 being jammed in a user's pocket or purse while the user is moving around in way that creates such intermittent stuck key conditions. When all keys are released, operation is again restored; and XPBLED1B and XPBLED2B, pins 36 and 37 of IC 50, will indicate battery status for six seconds.

Figure 9:
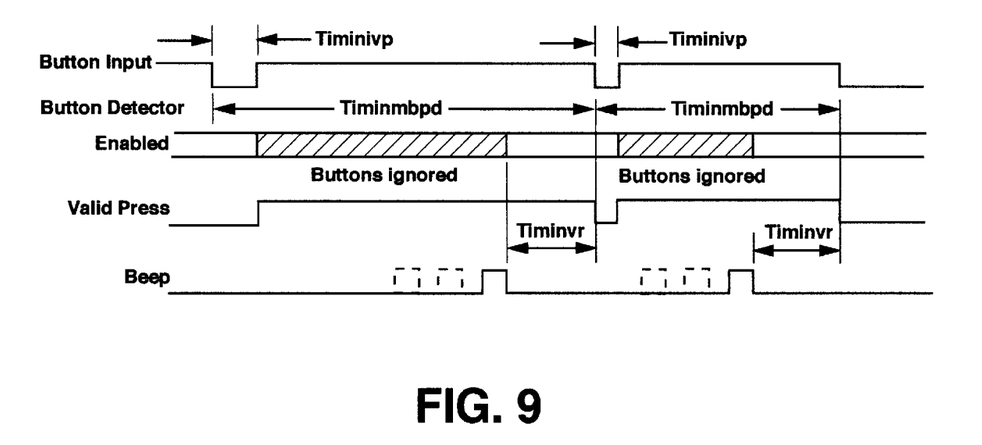
FIG. 9 is a timing diagram illustrating a timed sampling key debouncing scheme implemented in the integrated circuit of FIG. 8.

IC 50 also preferably is provided with key debouncing capability, well known to those of ordinary skill in the art, associated with key input pins 8–17 to IC 50. In one embodiment, IC 50 employs a timed sampling scheme to debounce and add noise immunity to key switches. In accordance with this timed sampling scheme, various minimum time intervals associated with key depression are defined, as shown in the timing diagram of FIG. 9. The various time intervals identified in FIG. 9 are defined as set forth in the following Table 3:

TABLE 3

| TIME INTERVAL DESIGNATION | VALUE (in milliseconds) | DESCRIPTION |
|---|---|---|
| Tminivp | 26 | Minimum time for initial valid press |
| Tminimvp | 16 | Minimum time for multiple valid presses |
| Tminvr | 120 | Minimum time for valid release |
| Tminibpd | 721 | Minimum delay (worst case) between initial button presses |
| Tminmbpd | 561 | Minimum delay (worst case) between multiple button presses |

Telemetry

Downlink telemetry consists of 33 RF bursts, as determined by the serial data programmed into the ROM of IC 50. The first RF burst is a start burst, the rest are data bits. Programming information is encoded serially to implanted device 44 via pulse interval modulation, which is well known in the art. Data is encoded by the time between falling edges of transmitted RF bursts.

In the presently preferred embodiment of the invention, the 32 downlink bits B0 through B31 are defined as set forth in the following Table 4:

TABLE 4

| DESCRIPTION | BIT NOS. | VALUE (HEX) | | |
|---|---|---|---|---|
| Access code | B0–B7 | varies with device | | |
| Parameter code | B8–B15 | | INC | DEC |
| | | Rate | 3C | 3D |
| | | Pulse Width | 4C | 4D |
| | | Amplitude | 5C | 5D |
| | | ON/OFF = 60 | | |
| Parameter value | B16–B23 | ON = 01 | | |
| | | OFF = 00 | | |
| | | INC/DEC = don't care | | |
| Error check word | B24–B31 | varies with transmission | | |

The error check word is determined by calculation of the parameter and value codes only. Starting with the least significant bit (LSB) of the parameter, each parameter and value bit is sequenced through a cyclic redundancy check (CRC) equation, in accordance with known practice.

Downlink is initiated by depressing any of the four user keys 19, 20, 21, or 22. Depression of any key shorts a respective pin of IC 50 to NVDD. If two or more keys are depressed simultaneously, only one key will be recognized, with priority per the following Table 5:

TABLE 5

| PRIORITY | KEY |
|---|---|
| 1 | OFF (key 22) |
| 2 | DEC (key 20) |
| 3 | ON (key 21) |
| 4 | INC (key 19) |

If implanted device 44 is OFF, it will accept only the DEC (key 20) and ON (key 21) commands. If an unacceptable command is given, beeper 58 will beep three times. If an INC or DEC command is given (i.e., if keys 19 or 20, respectively, are depressed), and the parameter is already at its respective limit (programmed by the doctor, as previously described), beeper 58 will beep three times.

If any of the keys 19, 20, 21 or 22 remains depressed at the end of downlink, another downlink will be generated after a two-second delay. After this second downlink, downlink commands will be repeated once per second until the key is released. Generating repeated downlinks for INC and DEC keys 19 and 20 creates a parameter scrolling effect in implanted device 44 which is not undesirable, as the scrolling rate combined with the initial two-second delay prevents patients with poor finger dexterity from making too large of a parameter change. In this embodiment, downlink and uplink timings required by implanted device 44 prohibit repetition rates greater than once per second. However, in other embodiments this rate could be increased.

Once any key 19, 20, 21, or 22 has been depressed, a second press will not be acknowledged until 120 milliseconds after completion of the beeper function. This desensitizes the keys to prevent unwanted multiple keypresses from patients who have spasticity in their fingers.

The actual downlink signal will be delayed for approximately 150 milliseconds to provide time for the receiver chip to stabilize for uplink reception. This delay is only for the first downlink command when the programmer comes out of the sleep mode.

For uplink telemetry reception, IC U2 (see FIG. 7) is used. IC U2 is an off-the-shelf receiver chip, such as the Signetics #TDA3047. IC U2 responds to uplink signals such as those transmitted by the Medtronic Model 7425 Itrel™. IC U2 demodulates the digital bits in the uplink telemetry signal, and provides the demodulated bit stream to IC 50, at pin 22 (XRXDATA). IC 50 decodes the demodulated uplink code and then drives appropriate ones of LEDs 32, 34, or 36, and beeper 58. In the presently preferred embodiment, an uplink transmission consists of 19 total RF bursts from implanted device 44. The uplink transmission is sent from implanted device 44 12±4 mSec after completion of each downlink.

Uplink codes are accepted and processed following downlink whether downlink activation keys are subsequently released or remain depressed. IC 50 responds to data from the last correct uplink signal received if a key remains depressed. This allows LEDs 32, 34, and 36, and beeper 58 to function properly with the last uplink signal received if programmer 10 is removed from the implant site of implanted device 44 with the user's finger still on a key, still transmitting downlinks from too far a distance to be usable. LEDs 32, 34, 36, and 38 hold their indication status for six seconds after release of a key, to give the patient an opportunity to view them.

No uplink is transmitted by implanted device 44 if a bad access code is received (i.e., programmer 10 and implanted device 44 are incompatible), a bad error code is received, or an incorrect pulse interval (indicative of noise) is received.

It is possible that a valid downlink can be received and executed by implanted device 44, but a correct uplink is not subsequently received by programmer 10 due to electrical noise, radio-frequency interference, or quick removal of programmer 10 from the implant site. In these situations, no LED status will be indicated, except for programmer battery status LED 38, unless a previously received correct uplink has been retained as a result of scrolling. In nearly all programming conditions, the patient will feel the programmed change immediately; hence, LEDs 32, 34, 36, and 38, and beeper 58 are an added convenience to reconfirm what the patient already has sensed.

Uplink bits are encoded via pulse interval modulation. Data is encoded by the time between leading edges of transmitted RF bursts. In the presently preferred embodiment of the invention, the nineteen uplink bits have a format as set forth in the following Table 6:

TABLE 6

| DESCRIPTION | BIT NOS. | VALUE |
|---|---|---|
| Synchronization bits | B0–B6 | 1 1 1 1 1 1 0 |
| Output state | B7 | ON = 1 |
| | | OFF = 0 |
| Invalid Command | B8 | INVALID = 1 |
| | | VALID = 0 |
| Implanted device battery status | B9–B10 | UNDEFINED = 0 0 |
| | | END OF LIFE = 10 |
| | | OKAY = 01 |
| | | LOW = 11 |
| Reserved for physician programmer | B11–B12 | don't care |
| Repeat | B13–B19 | Repeat of B7–B12 |

IC 50 senses uplink synchronization bits by looking for a logic one, and then waiting past the remaining ones until a zero is detected. Then, IC 50 accepts and processes subsequent data. This means that if some of the first ones are uplinked and missed due to receiver gain control stabilization, uplink can still be properly received.

Regarding LEDs 32, 34, 36, and 38, activation thereof is used to provide a visual indication of programming events. Programmer battery status LED 38 is activated whenever any key is depressed. The remaining LEDs 32, 34, and 36 are activated following the receipt of an uplink signal, with particular ones of LEDs 32, 34, and 36 lighting based upon the particular uplink signal data. Once activated, LEDs 32, 34, 36, and 38 remain on for six seconds after any key release. After this six-second time-out has expired, IC 50 enters a standby mode until a new key-press occurs. This advantageously minimizes power consumption during standby to conserve battery life.

As previously noted, if a key 19, 20, 21, or 22 is held depressed after programmer 10 is removed from the implant site, and one or more valid uplinks have been received, LEDs 32, 34, and 36 will indicate status based upon the last good uplink received. If any key 19, 20, 21, or 22 is subsequently pressed before a prior six-second LED timeout has expired, any of the LEDs 32, 34, 36, or 38 that were on as a result of the first key depression will remain on until updating upon completion of receipt of a valid uplink. If an unsatisfactory uplink or no uplink is received, only Programmer Battery Status LED 38 will be active. Programmer Battery Status LED 38 and implantable device battery status LED 36 light to indicate a good respective battery, blink at a rate of 2 to 4 times per second if the respective battery is low, and remain off if the battery is at EOL.

Although the presently disclosed embodiment of the invention utilizes a custom IC to control its operation as described above, it is contemplated that other implementations would be equally suitable. For example, it is believed that the present invention could be implemented using a general purpose microcontroller, microprocessor, or the like. Moreover, it is believed that those of ordinary skill in the art having the benefit of this disclosure would be readily able to realize a custom integrated circuit to implement the invention as described.

From the foregoing detailed description of a particular embodiment of the invention, it should be apparent that a patient programmer for facilitating patient control over an implanted device has been disclosed. Although a particular embodiment of the invention has been described herein in some detail, it is to be understood that this has been done solely for the purpose of illustration the invention in its various aspects, and is not intended to be limiting with respect to the scope of the invention. It is contemplated that various substitutions, alterations, and/or modifications, including but not limited to those specifically discussed herein, may be made to the disclosed embodiment without departing from the spirit and scope of the invention as defined in the appended claims, which follow.

What is claimed is:

1. A portable patient programmer for an implanted device, said programmer comprising:
    a main housing, configured to be held in a user's hand;
    a battery, disposed within said housing;
    a plurality of user key, disposed on said main housing;
    at least one visual indicator, disposed within said main housing and visible from outside said main housing;
    an audio indicator, disposed within said main housing and audible from outside said main housing;
    a telemetry receiver circuit, disposed within said housing and operative to receive uplink telemetry signals from said implanted device;
    a telemetry transmitter circuit, disposed within said housing, for transmitting said downlink operational command and parameter signals to said implanted device;
    a control circuit, disposed in said main housing and coupled to said user key, said visual indicators, said audio indicator, and said battery, said control circuit responsive to actuation of each of said key to control said transmitter circuit to transmit a predetermined one of said command and parameter signals to said implanted device wherein said control circuit is further responsive to continuous depression of one of said plurality of keys for longer than a first predetermined period of time during which none of said uplink signals is received by said receiver circuit to disable said transmitter circuit until said at least one key has been released.

2. A programmer in accordance with claim 1, wherein said control circuit is further responsive to the failure of said receiver circuit to receive an uplink telemetry signal after depression of one of said plurality of key following said second predetermined period of time to disable said transmitter circuit for a third predetermined period of time.

3. A programmer in accordance with claim 2 wherein said second predetermined period of time is less than said first predetermined period of time.

4. A programmer in accordance with claim 1, further comprising:
    an external antenna connector, disposed on said main housing and adapted to receive a mating connector from an external antenna.

5. A programmer in accordance with claim 1, wherein said programmer is operable to transmit a subset of said plurality of command and parameter signals.

6. A portable patient programmer for an implanted device, said programmer comprising:
    a main housing, configured to be held in a user's hand;
    a battery, disposed within said housing;
    at least one user key, disposed on said main housing;
    a telemetry receiver circuit, disposed within said housing and operative to receive uplink telemetry signals from said implanted device;
    a telemetry transmitter circuit, disposed within said housing, for transmitting downlink operational command and parameter signals to said implanted device;
    a control circuit, disposed in said main housing and coupled to said at least one user key, and said battery, said control circuit responsive to actuation of each of said at least one user key to control said transmitter circuit to transmit a predetermined one of said command and parameter signals to said implanted device, said control circuit being further responsive to continuous depression of one of said at least one user key for longer than a first predetermined period of time during which none of said uplink signals is received by said receiver circuit to disable said transmitter circuit until said at least one key has been released.

7. A programmer in accordance with claim 6, further comprising at least one visual indicator disposed within said main housing and visible from outside said main housing.

8. A programmer in accordance with claim 7, wherein said at least one visual indicator is a light-emitting diode, and wherein said control circuit is responsive to receipt, by said receiver circuit, of a predetermined uplink telemetry signal, to activate said visual indicator for a predetermined period of time.

9. A programmer in accordance with claim 6, further comprising an audio indicator disposed within said main housing and audible from outside said main housing.

10. A programmer in accordance with claim 6, wherein after said at least one key has been released said control circuit is further responsive to a next continuous depression of one of said at least one key for longer than a second predetermined period of time during which none of said uplink signals is received by said receiver circuit to disable said transmitter circuit until said at least one key has been released.

11. A programmer in accordance with claim 10 wherein said second predetermined period of time is less than said first predetermined period of time.

12. A method of controlling a portable patient programmer for an implanted device, the programmer having a main housing configured to be held in a user's hand, a battery disposed within the housing, at least one user key disposed on the main housing, a telemetry receiver circuit disposed within the housing and operative to receive uplink telemetry signals from the implanted device, a telemetry transmitter circuit disposed within the housing for transmitting downlink operational command and parameter signals to the implanted device, a control circuit disposed in the main housing and coupled to the at least one user key and the battery, the method comprising the steps of:

a) actuating a user key;

b) transmitting a predetermined one of the command and parameter signals to the implanted device in response to step a);

c) continuously actuating the user key in step a) for longer than a first predetermined period of time during which none of the uplink signals from the implanted device are received by the receiver circuit to disable the transmitter circuit until the user key in step a) has ceased to be actuated.

13. A method in accordance with claim 12, further comprising the step of activating an indicator for a predetermined period of time in responsive to receipt, by the receiver circuit, of a predetermined uplink telemetry signal.

14. A method in accordance with claim 13 wherein the step of activating an indicator includes the step of activating a visual indicator.

15. A method accordance with claim 13 wherein the step of activating an indicator includes the step of activating an audio indicator.

* * * * *